United States Patent [19]

Man et al.

[11] Patent Number: 5,670,378
[45] Date of Patent: Sep. 23, 1997

[54] METHOD FOR TRACE OXYGEN DETECTION

[75] Inventors: Kin Fung Man, Arcadia; Said Boumsellek, Altadena; Ara Chutjian, La Crescenta, all of Calif.

[73] Assignee: The United States of America as represented by the Administrator of the National Aeronautics and Space Administration, Washington, D.C.

[21] Appl. No.: 392,575

[22] Filed: Feb. 23, 1995

[51] Int. Cl.⁶ ............................................. G01N 23/00
[52] U.S. Cl. ..................... 436/136; 436/116; 436/134; 436/138; 436/173; 250/282; 250/288
[58] Field of Search .................... 250/282, 288; 436/116, 134, 136, 138, 173

[56] References Cited

U.S. PATENT DOCUMENTS

| | | | |
|---|---|---|---|
| 2,761,975 | 9/1956 | Weisz | 250/282 |
| 3,621,240 | 11/1971 | Cohen | 250/282 |
| 3,742,213 | 6/1973 | Cohen et al. | 250/288 |
| 3,866,041 | 2/1975 | Attia | 250/247 |
| 4,158,775 | 6/1979 | Chutjian et al. | 250/423 P |
| 4,239,967 | 12/1980 | Carr et al. | 250/282 |
| 4,261,698 | 4/1981 | Carr et al. | 23/232 |
| 4,649,273 | 3/1987 | Chutjian et al. | 250/251 |
| 4,649,278 | 3/1987 | Chutjian et al. | 250/423 |
| 4,757,198 | 7/1988 | Korte et al. | 250/282 |
| 4,771,172 | 9/1988 | Weber-Grabau et al. | 250/282 |
| 4,855,594 | 8/1989 | Kimock et al. | 250/282 |
| 4,902,642 | 2/1990 | Chutjian et al. | 437/239 |
| 4,933,551 | 6/1990 | Bernius et al. | 250/288 |
| 4,963,735 | 10/1990 | Okamoto et al. | 250/288 |
| 4,975,576 | 12/1990 | Federer et al. | 250/282 |
| 5,053,343 | 10/1991 | Vora et al. | 436/173 |
| 5,097,124 | 3/1992 | Devienne | 250/283 |
| 5,175,431 | 12/1992 | Eisele et al. | 250/288 |
| 5,218,203 | 6/1993 | Eisele et al. | 250/288 |
| 5,256,874 | 10/1993 | Chutjian | 250/288 |
| 5,291,017 | 3/1994 | Wang et al. | 250/292 |
| 5,300,773 | 4/1994 | Davies | 250/286 |
| 5,304,797 | 4/1994 | Irie et al. | 250/287 |
| 5,347,828 | 9/1994 | Boumsellek et al. | 250/427 |
| 5,412,207 | 5/1995 | Micco et al. | 250/282 |
| 5,432,343 | 7/1995 | Gulcicek et al. | 250/282 |
| 5,442,175 | 8/1995 | Dawson | 250/282 |

OTHER PUBLICATIONS

Bernius et al. "Application of Reversed Electron Attachment for Ultrasensitive Detection of Thermal Electron–Attaching Molecules: $CCl_4$ & $C_6H_5NO_2$" Anal. Chem. 1990, 62, 1345–1349.

Bernius et al. "Pulsed High Current in Line Reversal Electron Attachment Detector". J. Appl. Phys. 66(7) Oct. 1, 1989 pp. 2783–2788.

McLuckey et al "Atmospheric Sampling Glow Discharge Ionization Source for the Determination of Trace Organic Compounds in Ambient Air" Anal. Chem. 1988, 60, 2220–2227.

Boumsellek et al "Increased Response of the Reversal Electron Attachment Detector & Modeling of Ion Spaced–Charged Effects" Anal. Chem. 1992, 64, 2096–2100.

(List continued on next page.)

*Primary Examiner*—Jill Warden
*Assistant Examiner*—Sharidan Carrillo
*Attorney, Agent, or Firm*—John H. Kusmiss

[57] ABSTRACT

Trace levels of molecular oxygen are measured by introducing a gas containing the molecular oxygen into a target zone, and impacting the molecular oxygen in the target zone with electrons at the $O^-$ resonant energy level for dissociative electron attachment to produce $O^-$ ions. Preferably, the electrons have an energy of about 4 to about 10 eV. The amount of $O^-$ ions produced is measured, and is correlated with the molecular oxygen content in the target zone. The technique is effective for measuring levels of oxygen below 50 ppb, and even less than 1 ppb. The amount of $O^-$ can be measure in a quadrupole mass analyzer. Best results are obtained when the electrons have an energy of about 6 to about 8 eV, and preferably about 6.8 eV. The method can be used for other species by selecting the appropriate electron energy level.

12 Claims, 4 Drawing Sheets

OTHER PUBLICATIONS

Krishnakumar et al. "Dissociative Attachment of Electrons to $N_2O$" Physical Review A, 41, 5, Mar. 1, 1990, 2445–2457.

P. K. Sharma, 4th Int. Conf. on *Experimental Methods for Microgravity Materials Science Research, Kinetic Considerations in Oxide Monolayer Formation on Metals and Implication to Microgravity Experiments Dealing With Metallic Melts*, Ed. R. A. Schiffman, A Publication of the Minerals Metals & Materials Society, Warrendale, Pennsylvania 127–132 (1992).

P. K. Sharma and P. K. Seshan, *Activation of Copper Dispersed On A Zeolite For Oxygen Sorption, Chemically Modified Oxide Surfaces*, vol. 3, Eds. D. E. Leyden and W. T. Collins, Gordon and Breach, New York, 65–80 (1990).

P. K. Sharma and P. K. Seshan, *Copper Oxide Modified Carbon Molecular Sieves for Selective Oxygen Removal, Gas Separation & Purification*, vol. 4, Butterworth–Heinemann Ltd, 1990, pp. 203–207.

S. Boumsellek and A. Chutjian, *Increased Response of the Reversal Electron Attachment Detector and Modeling of Ion Space–Charge Effects*, Anal. Chem. Instrum. 64 (1992), 2096–2100.

M. T. Bernius and A. Chutjian, *High–voltage, full–floating 10–MHz square–wave generator with phase control*, Rev. Sci. Instrum. 60(4), Apr. 1989, 779–782.

R.K. Asundi et al., *Electron Attachment and Ionization in Oxygen, Carbon Monoxide and Carbon Dioxide*, Proc. Phys. Doc., 1963, vol. 82, 967–978.

G. J. Schulz, *Cross Sections and Electron Affinity for $O^-$ Ions From $O_2$, CO, and $CO_2$ by Electron Impact*, Phys. Rev., vol. 128, No. 1, Oct. 1962, pp. 178–185.

S. Boumsellek and A. Chutjian, *Pulsed, gridded electron reversal ionizer*, Rev. Sci. Instrum. 64(5), May 1993, 1135–1139.

O. J. Orient and A. Chutjian, Phys. Rev. A 34 1841 (1986).

METHOD FOR TRACE OXYGEN DETECTION

ORIGIN OF THE INVENTION

The invention described herein was made in the performance of work under a NASA contract, and is subject to the provisions of Public Law 96-517 (35 U.S.C. 202) in which the Contractor has elected not to retain title.

TECHNICAL FIELD

The present invention relates to detection of trace levels of gases such as oxygen.

BACKGROUND

Chemical processes can take place in the presence of trace amounts of oxygen, i.e., those measured in the parts per billion (ppb). In some processes it is desirable that the oxygen be present, and in other processes the oxygen is an undesirable contaminant. Among processes that can take place at trace levels of oxygen include crystal growth, semiconductor fabrication, pharmaceutical manufacture, materials purification, and chamberless processes.

For example, during those processes, oxygen can lead to rapid surface oxide formation and thereby adversely affect the properties of materials or the quality of parts produced. If during the fabrication of semiconductor devices, oxygen in the processing chamber is present at a level of parts per billion at 1000° C., after only about 10 seconds, an oxide layer can form on the surface of the semiconductor.

In semiconductor device fabrication, low levels of oxygen can be present as a contaminant, as a result of outgassing from hot surfaces or as part of the impurities present in gas introduced into a process chamber.

Control and monitoring of oxygen level are crucial to the success of such processes as containerless processing and semiconductor device fabrication. Although much effort has been expended in reducing oxygen concentration, by using oxygen sorbents for example, the viability of such sorbents depends on the ability to accurately measure oxygen concentrations.

Existing commercial instruments are unsatisfactory for monitoring, controlling, and measuring oxygen contents lower than about 50 ppb. Most commercial instruments for trace oxygen measurement use an electrochemical cell as a sensor element, either a solid electrolytic detector or liquid electrolytic detector. The solid detectors have an oxygen detection limit of about 50 ppb, and the liquid detectors have only a slightly lower limit. While an atmospheric pressure ionization mass spectrometer has the potential of measuring below 1 ppb level for some gas species, it has not been tested systematically for oxygen.

Accordingly, there is a need for an instrument which can be made commercially available for detecting trace quantities of oxygen, i.e., levels of oxygen less than 50 ppb, and preferably less than 1 ppb.

STATEMENT OF INVENTION

The present invention is directed to a method that solves the above-identified need. According to the method of the present invention, the molecular oxygen content of a gas is measured by introducing the gas into a target zone that is under vacuum, i.e., a vacuum chamber, and impacting the molecular oxygen in the target zone with electrons having an energy of from about 4 to about 10 eV to yield dissociative electron attachment to produce $O^-$ ions. The amount of $O^-$ ions produced is then measured. The presence of molecular oxygen is inferred from detection of the product $O^-$ ions.

This method is effective due to the use of electrons having the selected energy level, because the electron attachment cross section is greatly enhanced at the resonant energy of the reaction, i.e., from about 4 to about 10 eV. This yields a high level of $O^-$ ions, yielding high sensitivity and a low detection limit.

To measure the $O^-$ produced, the $O^-$ ions are extracted from the target zone and introduced into a device such as a quadrupole mass analyzer, where the mass analyzer is tuned to an m/e (mass/electron) ratio of 16.

The amount of molecular oxygen in the target zone is determined by correlation with the amount of $O^-$ detected in the mass analyzer.

Typically the vacuum in the target zone is at least $10^{-5}$ torr.

Typically in the process species other than $O^-$ are produced, such as $O_2^-$, and other trace gases such as $H_2$ may be present. To measure the $O^-$ produced, the contaminants are filtered out before the amount of $O^-$ produced is measured.

The amount of $O_2$ converted to $O^-$ is maximized when the electrons have an energy of about 6 to 8 eV, and most preferably about 6.8 eV, i.e., an energy level at the resonant energy level of the formation of $O^-$ from $O_2$.

The method is also effective for detecting other molecular species that require electrons having an energy of at least 4 eV for dissociative electron attachment.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

The present invention is directed to a method for measuring very low levels of molecular oxygen with great accuracy, levels less than 50 ppb, and levels even less than 1 ppb. According to this method, molecular oxygen is impacted in a target zone with electrons having an energy of from about 4 to about 10 eV, resulting in dissociative electron attachment that produces $O^-$ ions. The $O^-$ ions produced are then measured, and can be correlated with the amount of molecular oxygen in the target zone.

The present invention utilizes resonant attachment of electrons, which is based on electron attachment to a target at a particular resonance energy. The resonant attachment is followed by mass detection of the negative $O^-$ ion species. This technique utilizes the fact that the attachment cross section (i.e., probability of producing O⁻ ions) is greatly enhanced at the resonance energy.

Two principal modes of electron attachment (dissociative and nondissociative) are possible with the bombardment of a molecule, denoted by AB, by resonant-energy electrons:

and

When $AB=O_2$, reactions (1) and (2) are the following two reactions, respectively:

In nondissociative electron attachment the parent negative ions (AB⁻) formed are normally stable with respect to dissociation and autodetachment. The parent ions (AB⁻) are then detected, allowing unambiguous determination of the molecular species AB. In dissociative electron attachment the parent molecules (AB) are inferred from detection of the product ions (B⁻ in this example).

For molecular oxygen, the dissociative electron attachment process is reaction (4), producing O⁻.

Figure 1:
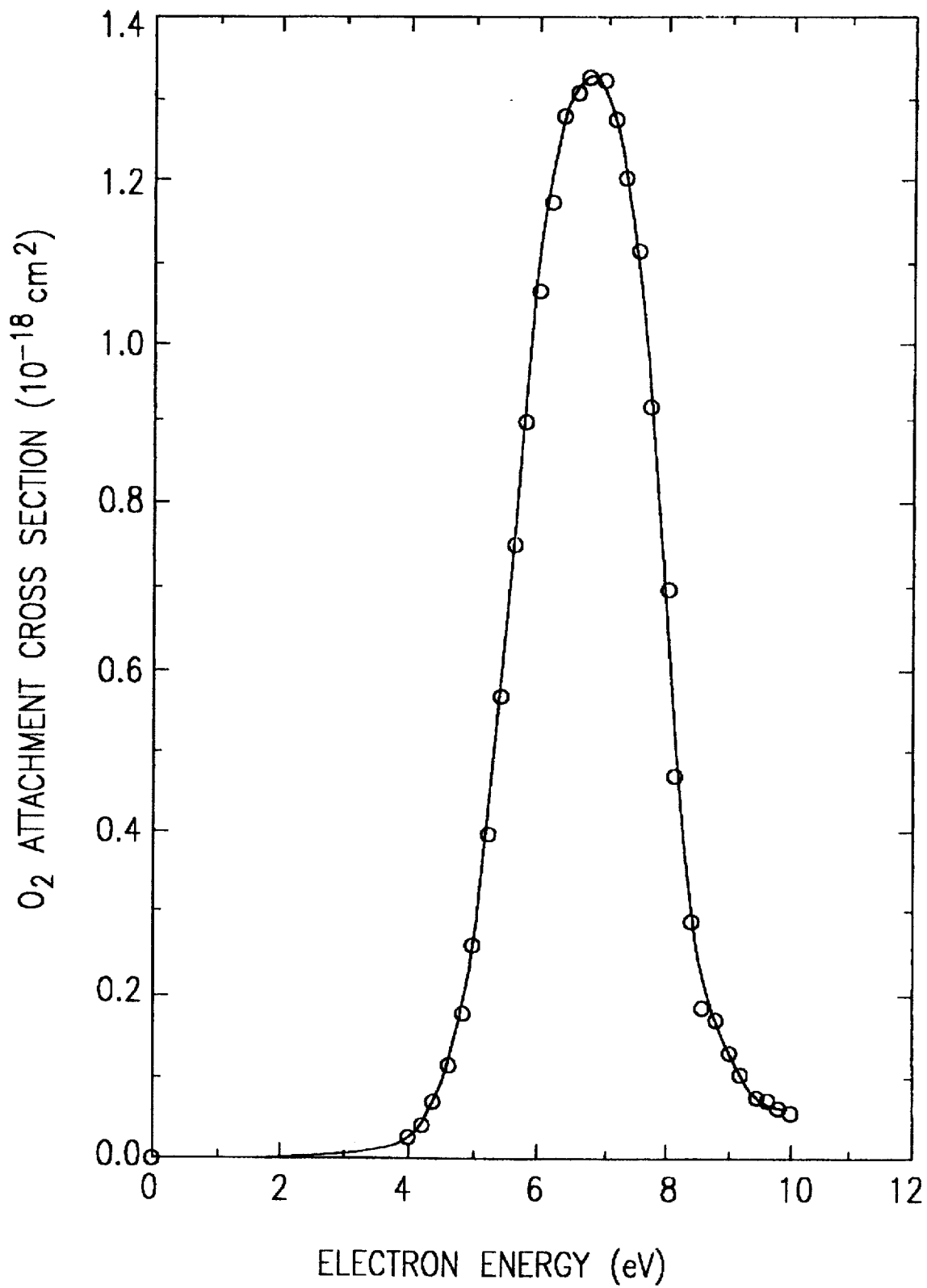
FIG. 1 graphically presents the amount of $O^-$ produced from $O_2$ by impacting the $O_2$ with electrons, as a function of the energy of the electrons.

The resonance energy for O⁻ formation by electron impact of molecular oxygen is about 6.8 eV, as shown in FIG. 1 (see R. K. Asundi et al., Proc. Phys. Soc., 82, 967 (1963)) with a cross section of about $1.34 \times 10^{-18}$ cm². The detection of O⁻ is used in this invention as signature for the presence of molecular oxygen.

The following analysis indicates that, according to the present invention, the method is at least theoretically capable of detecting concentrations of molecular oxygen at the sub-ppt (sub-parts per trillion) level, and as demonstrated by the examples discussed below, has been demonstrated to be effective at less than 1 ppb (parts per billion).

In order to evaluate the capability of this technique and to obtain an estimate of its detection limit, we conducted the following calculation based on realistic experimental parameters using a quadrupole mass analyzer for O⁻ detection. The detected O⁻ signal count rate, S (in Hz), from electron attachment of $O_2$ (in single collision conditions) at the resonance energy is given by:

$$S(Hz) = \kappa \cdot n_T \cdot V \cdot n_e \cdot v_e \cdot \sigma(E) \quad (5)$$

where

E is the electron energy, at the resonant dissociative attachment energy of oxygen, =6.8 eV;

σ(E) is the cross section for O⁻ production at the resonance energy, $=1.34 \times 10^{-7}$ cm²;

$v_e$ is the electron velocity at the resonance energy (6.8 eV) $=15.4 \times 10^7$ cm.s⁻¹;

$n_e$ is the electron density, estimated to be $2.6 \times 10^8$ cm⁻³ for a 50 μA beam;

V is the size of the collision region, which is a spherical volume (see S. Boumsellek and A. Chutjian, Rev. Sci. Instrum., 64, 1135 (1993), estimated to be $\sim 2 \times 10^{-2}$ cm³;

$n_T$ is the molecular oxygen density at room temperature, the quantity to be determined; and κ is the transmission coefficient corresponding to the quadrupole mass efficiency and the loss of ions during extraction, estimated to be ~0.005. This value assumes a 50% duty cycle for the analyzer.

Assuming a signal rate of 100 Hz is necessary for a reasonable signal-to-noise ratio, we calculated from equation (5) the corresponding value of $n_T$ in the atmosphere to be detected:

$$n_T = 1.86 \times 10^7 cm^{-3}$$

This corresponds to a fractional concentration in air of:

$$C = 0.68 \times 10^{-12}$$

Thus, our method is capable, theoretically, of detecting concentrations in the sub-ppt level.

Among the apparatus suitable for practicing the present method, a preferred apparatus is a reversal electron attachment detector capable of producing electrons having a desired energy effective for producing O⁻ ions. As shown in FIG. 1, electrons need to have an energy of from about 4 to about 10 eV, more preferably from about 6 to about 8 eV, and most preferably about 6.8 eV.

Suitable instrumentation is described in S. Boumsellek and A. Chutjian, "Pulsed, Gridded Electron Reversal Ionizer", Rev. Sci. Instrum., 64(5), May 1993, pages 1135–1139 and U.S. Pat. No. 5,256,874, both of which documents are incorporated herein by reference. Such an apparatus is shown schematically in FIG. 2.

Figure 2:
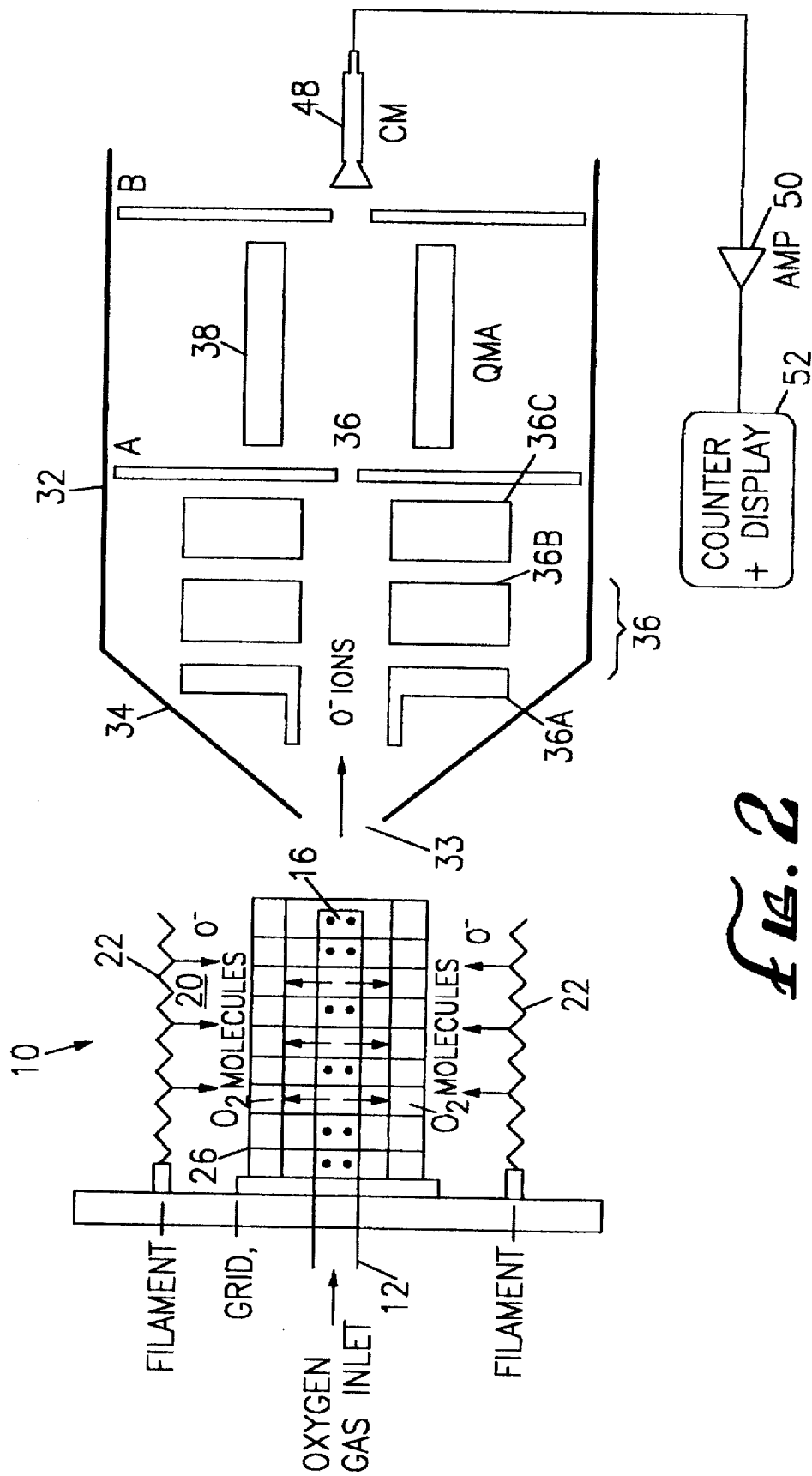
FIG. 2 is a schematic diagram of an apparatus suitable for practicing the process of the present invention.

With reference to FIG. 2, a gridded electron reversal ionizer 10 has an oxygen gas inlet 12 under vacuum, typically at least $10^{-4}$ torr, up to about $10^{-7}$ torr, and preferably at least $10^{-5}$ torr. Gases at higher pressure, near ambient pressures can be sampled by use of an atmospheric interface or trap, such as a rotary vapor trap available from Ion Track Instruments of Billington, Mass.

The gas sample containing oxygen is provided to a central electrode 16 which is an electrically isolated perforated stainless tube of a length of about 1.5 inches, a diameter of about 0.25 inches, and with about 100 holes drilled therein, each having a diameter of about 0.01 inch. The gas containing $O_2$ then flows through the holes in the electrode into a central chamber or target zone 20 of the ionizer 10 with relatively low kinetic energy typical of gases at room temperature.

At the same time, electrons are generated from a filament 22, which can be any convenient source of electrons capable of high electron emissivity at the highest pressure in the device, e.g., $10^{-4}$ torr, and which is not contaminated by oxygen or any other trace species that can be present. A suitable electron source is thoriated iridium filament of the type used in a Bayard-Alpert ionization gauge available from Varian Associates of Palo Alto, Calif. as Model No. 0581-L5151-301 or from Granville-Phillips Corp. of Boulder, Colo., as Model No. 274025. The potential applied across filament 22 is controlled to vary the current of the cloud of electrons generated therefrom.

The gridded electron reversal ionizer 10 can be operated in a pulsed extraction operation, in which a grid electrode 26 is rapidly biased negatively to prevent the electrons from reaching the electrode 26, while at the same time pulsing an extraction plate 32 having an extraction aperture 33 positive to draw out the negative ions formed near the central electrode 16. The kinetic energy of the electrons near the surface of the central electrode 16 is controlled by adjusting the potentials applied to the grid electrode 26 and the central electrode 16.

Alternatively, the gridded electron reversal ionizer 10 can be operated in a continuous mode, but the electron energies inclusion volume are less well defined in that operating mode.

The filament 22 can conventionally be formed into a hollow cylindrical shape, a hollow conical shape, or any other convenient shape enclosing the central cavity or chamber 20. A cylindrical, symmetrical arrangement has the advantage that the electrical potentials are substantially uniform. The filament 22 surrounds the grid electrode 26 which has the same shape as the filament 22, but a smaller diameter. The filament 22 and grid electron 26 both surround the central electrode 16.

The potentials of the filament 22 and the grid electrode 26 are controlled so that the cloud of electrons generated from the filament 22 are accelerated by the grid electrode 26 towards the central electrode 16. The negative potential of the central electrode 16 is controlled by a control system (not shown) so that in the volume adjacent the central electrode 16, the acceleration of the electrons is reduced to zero or near zero velocity, with the result that electrons having the desired energy, i.e., from about 4 to about 10 eV are present to collide with molecular oxygen emerging from the central electrode holes in the target zone 20. This produces negative $O^-$ ions which are then analyzed to detect and measure the presence of molecular $O_2$ at very low concentrations.

The formed $O^-$ ions are extracted and formed by an extraction cone 34 and a first lens 36a of a three lens ion extraction system 36, preferably an Einzel lens system, comprising, sequentially, the first lens 36a, a second lens 36b, and a third lens 36c. The focused $O^-$ ions are then passed through the aperture 33 in the plate 32, which can be the external wall of a mass analyzer, such as a magnetic or quadrupole mass analyzer 38.

The negative $O^-$ ions can be extracted by means of a pulsing operation as described, for example, in U.S. Pat. No. 4,933,551, or by controlling the potential of the extraction plate 32 to accelerate the negative ion cloud towards the mass analyzer 38 through the aperture 36.

The $O^-$ ions in the mass analyzer can be detected with a channel multiplier 48, where the signal generated is amplified by an amplifier 50, and then counted by a single-channel scaler with scaler 52, preferably having a variable counting time, and then displayed.

The mass analyzer is tuned to an m/e ratio of 16 to filter out ionic species produced in the target zone and other contaminants introduced into the target zone with the $O_2$.

A suitable mass analyzer is available from Extrel of Pittsburgh, Pa., Model No. 011-1.

Features of the present invention will be better understood by the following examples.

EXAMPLE 1

The apparatus shown in FIG. 2 is used to detect the presence of oxygen.

The electron acceleration and ion extraction were operated in a pulsed mode with a 50% duty cycle at a repetition rate of 9 kHz. During the "electrons ON" cycle $O^-$ ions were produced and during the "electron OFF" cycle, $O^-$ ions were measured. During the ON cycle, a 12 volt potential was applied to the grid 26. Electrons from the filament 22 were accelerated through the grid 26 towards the grounded central electrode 16 to produce $O^-$ ions. During this ON cycle, the voltages on the extraction cone 34 and the first lens 36a were held at ground so that fields from these elements did not interfere with fields in the collision region and did not disturb the motion of the low energy electrons.

During the "electrons OFF" (i.e., "ions ON") cycle, the voltage at the grid 26 was reduced to −0.05 V and the voltages on the extraction cone 34 and the first lens 36a were raised to 50 V. The voltages on the second lens 36b and the third lens 36c were set at 170 V and 40 V, respectively (not pulsed), to extract the $O^-$ ions from the collision region.

Figure 3:
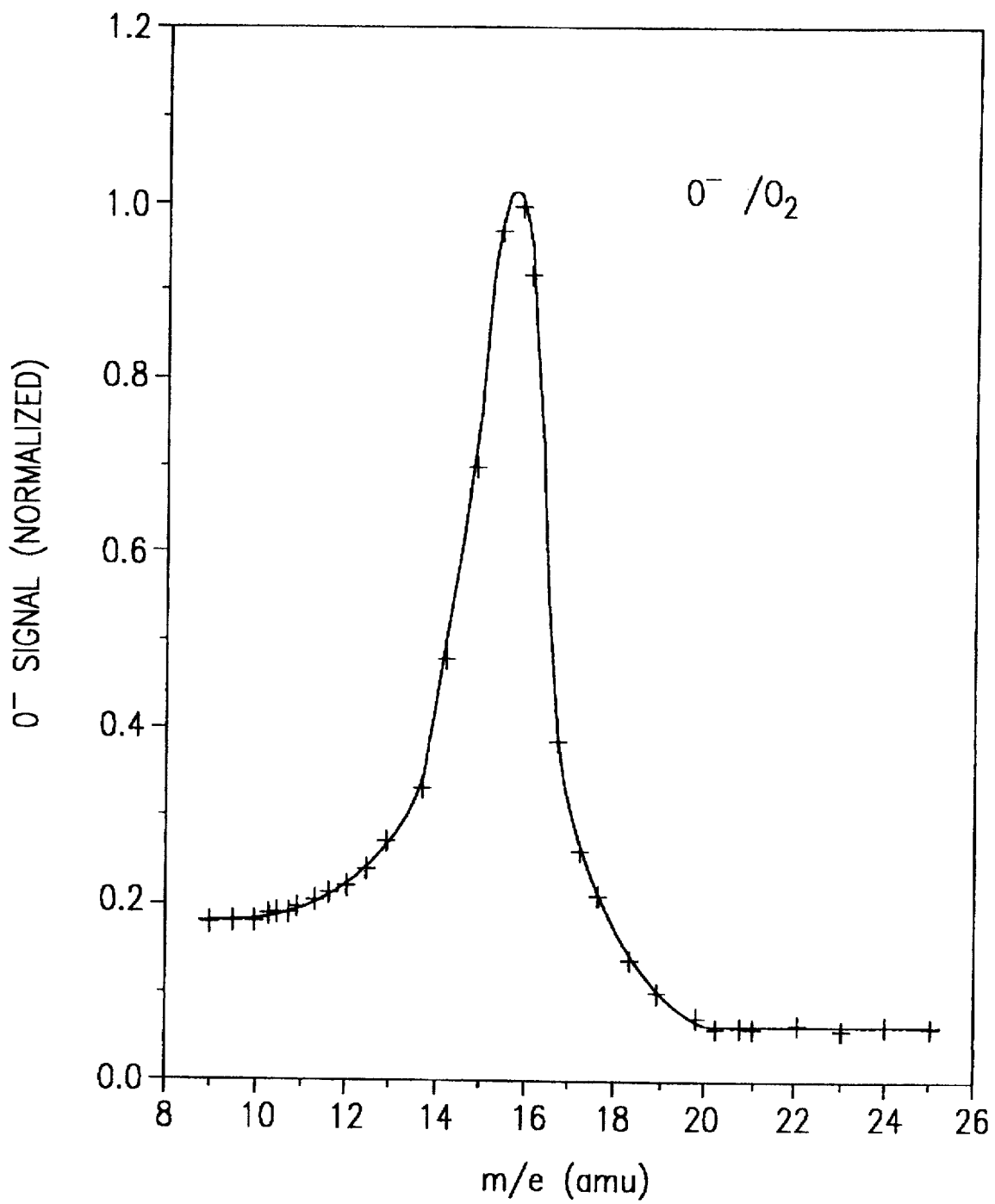
FIG. 3 is a mass spectrum of dissociative electron attachment of $O_2$, showing a peak at m/e=16 corresponding to $O^-$.

A mass spectrum corresponding to the negative ions formed in dissociative electron attachment of oxygen was detected by the mass analyzer 38 and displayed in the display device 52. As shown in FIG. 3, the peak was clearly visible at m/e=16, corresponding to $O^-$.

EXAMPLE 2

This example shows that the method of the present invention can measure a wide range of $O_2$ concentrations including trace amounts of $O_2$.

The same equipment and method used for Example 1 were again used. Mixtures of $O_2$ and $N_2$ (99.99% purity) were produced at various fractional concentrations, measured by particle density, ranging from 1.0 (pure $O_2$) to $1 \times 10^{-10}$, in a stainless steel vacuum system. All ions were thoroughly outgassed to prevent contamination of the mixtures during preparation. The $O_2$-$N_2$ mixtures were transferred to the target region via an oxygen gas inlet which was kept at $2 \times 10^{-7}$ torr pressure.

Figure 4:
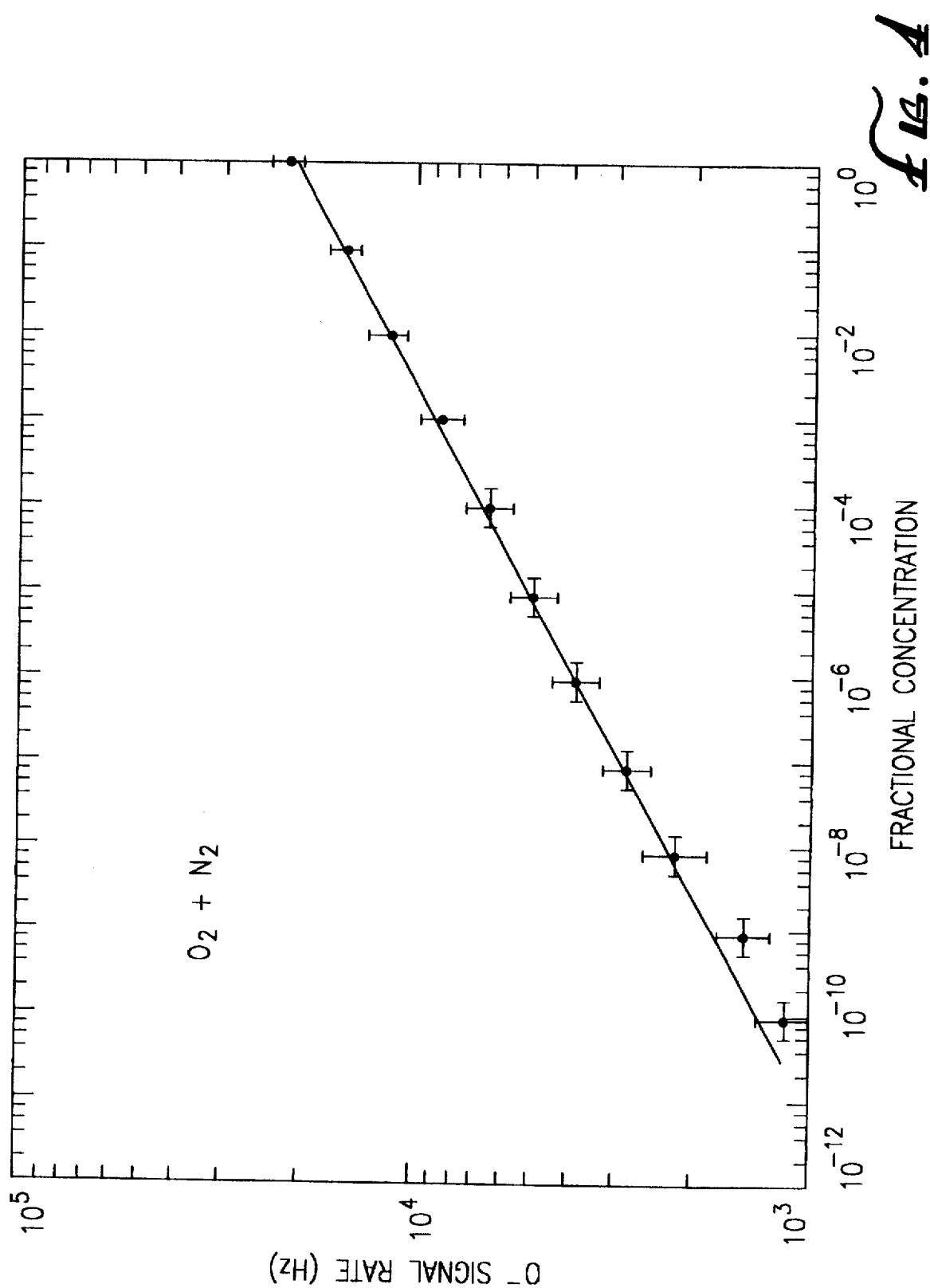
FIG. 4 is a sensitivity curve for detecting $O^-$ produced from varying concentrations of $O_2$ by using a process according to the present invention.

The $O^-$ signal was measured as a function of concentration and sensitivity was obtained from the slope utilizing a standard-additions plot. The results are shown in FIG. 4. Errors in the data represent the quadrature sum of the statistical counting error, and the error reading the pressure gauges used to make up each fraction. They are shown in FIG. 4 at the 1.7 σ (90%) confidence level. The $O^-$ signal S(Hz) has a maximum value S=21 kHz for pure oxygen, and then decreases uniformly to a value of S=1.2 kHz at oxygen concentration of $1 \times 10^{-10}$ (0.1 ppb).

As shown by FIG. 4, our method can be effectively used to measure oxygen concentrations of pure oxygen to levels less than 1 ppb. Moreover, it is believed that sensitivity can be improved by adding additional electron currents by using more filaments 22, and by increasing the efficiency of the ion extraction optics.

The present invention has significant advantages compared to conventional methods for measuring low concentrations of oxygen. For example, it is very accurate at very low concentrations, less than 1 ppb. It is simple, inexpensive, direct, and requires no chemicals. The method lends itself to automation for automatic and controlled detection and analysis of oxygen contaminants. Moreover, as shown by FIG. 4, it is useful over a wide range of concentrations.

Although the present invention has been described in considerable detailed with reference to certain preferred versions thereof, other versions are possible. For example, the present method can be used for gas species other than $O_2$. The success of the technique results from impacting the gas species with electrons having an energy level at the resonant energy of the ion species that is to be produced, to maximize the amount of molecules ionized to the desired ion species. The following table provides other exemplary uses of the present invention.

| GAS MOLECULE | DETECTABLE ION | RESONANT ENERGY (eV) | RANGE OF ENERGIES FOR ELECTRONS (eV) |
| --- | --- | --- | --- |
| NO | O⁻ | 8.5 | 7.5–10 |
| CO | O⁻ | 9.8 | 8–12 |
| $H_2$ | H⁻ | 12 | 11–13 |
| $CH_4$ | H⁻ | 10 | 4.5–12 |
| $CO_2$ | O⁻ | 8 | 6–10 |
| $H_2O$ | O⁻ | 11 | 7–14 |

Therefore, the spirit and scope of the appended claims should not be limited to the description of the preferred versions contained herein.

We claim:

1. A method for measuring an amount of molecular oxygen in a gas comprising the steps of:
   a) introducing a gas containing an amount of molecular oxygen into a target zone under vacuum;
   b) impacting the molecular oxygen in the target zone with electrons having an energy of from 4 to 10 eV for dissociative electron attachment to produce O⁻ ions;
   c) extracting the O⁻ ions from the target zone;
   d) introducing the extracted ions into a mass analyzer to determine an amount of O⁻ ions produced; and
   e) correlating the amount of O⁻ ions produced with the amount of molecular oxygen in the target zone.

2. The method of claim 1 wherein the vacuum in the target zone is at least $10^{-4}$ torr.

3. The method of claim 2 wherein the vacuum in the vacuum zone is at least $10^{-5}$ torr.

4. The method of claim 1 wherein the electrons have an energy of about 6 to about 8 eV.

5. The method of claim 4 wherein the electrons have an energy of about 6.8 eV.

6. The method of claim 1 wherein the amount of molecular oxygen in the target zone is less than 50 ppb.

7. The method of claim 6 wherein the amount of molecular oxygen in the target zone is less than 1 ppb.

8. The method of claim 1 comprising the additional step of tuning the mass analyzer to detect ions having an m/e value of 16.

9. The method of claim 1 wherein the step of impacting the molecular oxygen results in production of ionic species in addition to O⁻ ions, and wherein the mass analyzer is tuned to filter out said ionic species.

10. The method claim 1 wherein the step of introducing the molecular oxygen into the target zone results in introduction of at least one contaminant species into the target zone in addition to molecular oxygen, and wherein the mass analyzer is tuned to filter out said ionic species.

11. A method for measuring the content of gaseous molecular oxygen in a gas, the oxygen being capable of undergoing dissociative electron attachment to produce detectable O⁻ ions, the method comprising the steps of:
   a) introducing the gas containing an amount of molecular oxygen into a target zone;
   b) maintaining the target zone under vacuum;
   c) impacting the gas with electrons having an energy level of at least 4 eV and about equal to the resonant energy of the detectable O⁻ ions for dissociative electron attachment to the molecular oxygen to produce the detectable O⁻ ions;
   d) extracting the detectable O⁻ ions from the target zone; and
   e) correlating an amount of detectable O⁻ ions produced with the amount of molecular oxygen introduced into the target zone.

12. The method of claim 11 wherein, the target zone is maintained under a vacuum of at least $10^{-4}$ torr, and the electrons have an energy of from about 6 to about 8 eV.

* * * * *